United States Patent
Iwasaki et al.

(10) Patent No.: US 11,534,065 B2
(45) Date of Patent: Dec. 27, 2022

(54) CONTACT LENS AND COMMUNICATION SYSTEM

(71) Applicants: Sony Corporation, Tokyo (JP); Sony Semiconductor Solutions Corporation, Kanagawa (JP)

(72) Inventors: Masanori Iwasaki, Kanagawa (JP); Takayuki Hirabayashi, Tokyo (JP); Naoto Yamaguchi, Tokyo (JP); Tsukasa Yoshimura, Tokyo (JP); Masakazu Yajima, Kanagawa (JP); Fumiko Shiga, Tokyo (JP)

(73) Assignees: Sony Corporation, Tokyo (JP); Sony Semiconductor Solutions Corporation, Kanagawa (JP)

( * ) Notice: Subject to any disclaimer, the term of this patent is extended or adjusted under 35 U.S.C. 154(b) by 338 days.

(21) Appl. No.: 16/771,484

(22) PCT Filed: Nov. 1, 2018

(86) PCT No.: PCT/JP2018/040650
§ 371 (c)(1),
(2) Date: Jun. 10, 2020

(87) PCT Pub. No.: WO2019/116767
PCT Pub. Date: Jun. 20, 2019

(65) Prior Publication Data
US 2021/0085177 A1  Mar. 25, 2021

(30) Foreign Application Priority Data
Dec. 15, 2017 (JP) .............................. JP2017-240264

(51) Int. Cl.
| | | |
|---|---|---|
| G02C 7/04 | (2006.01) | |
| A61B 3/10 | (2006.01) | |
| A61B 5/00 | (2006.01) | |
| A61B 3/125 | (2006.01) | |
| A61B 3/00 | (2006.01) | |
| A61B 3/12 | (2006.01) | |

(Continued)

(52) U.S. Cl.
CPC ............ *A61B 3/125* (2013.01); *A61B 5/6821* (2013.01); *G02C 7/04* (2013.01); *A61B 3/0025* (2013.01);
(Continued)

(58) Field of Classification Search
CPC ......... G02C 7/04; G02C 11/10; A61B 5/6821; A61B 3/16; A61B 3/125; A61B 5/682
See application file for complete search history.

(56) References Cited

U.S. PATENT DOCUMENTS 10,478,104 B2 * 11/2019 Lamrani .............. A61B 5/6821
10,775,644 B2 * 9/2020 Pugh ................ B29D 11/00817
(Continued)

FOREIGN PATENT DOCUMENTS

| JP | 2011-515256 A | 5/2011 |
|---|---|---|
| JP | 2013-156632 A | 8/2013 |

(Continued)

OTHER PUBLICATIONS

International Search Report issued in International Patent Application No. PCT/JP2018/040650 dated Jan. 22, 2019 and English translation of same. 5 pages.

(Continued)

*Primary Examiner* — Xuemei Zheng
(74) *Attorney, Agent, or Firm* — K&L Gates LLP

(57) ABSTRACT

A contact lens according to an embodiment of the present disclosure includes a lens unit to be placed on an eyeball and a mesh-like or meandering linear communication electrode provided in all or a portion of the lens unit.

8 Claims, 13 Drawing Sheets

(51) Int. Cl.
*A61B 3/16* (2006.01)
*A61B 5/024* (2006.01)
*A61B 5/145* (2006.01)
*H04B 1/3827* (2015.01)
*B29D 11/00* (2006.01)

(52) U.S. Cl.
CPC .............. *A61B 3/1241* (2013.01); *A61B 3/16* (2013.01); *A61B 5/002* (2013.01); *A61B 5/02438* (2013.01); *A61B 5/14507* (2013.01); *A61B 5/14532* (2013.01); *A61B 5/14546* (2013.01); *A61B 5/6803* (2013.01); *B29D 11/00826* (2013.01); *H04B 1/385* (2013.01)

(56) References Cited

U.S. PATENT DOCUMENTS

2015/0362752 A1\* 12/2015 Linhardt .......... B29D 11/00048 349/13
2017/0235158 A1 8/2017 Markus et al.
2018/0160976 A1\* 6/2018 Park ............... C12Y 101/03004

FOREIGN PATENT DOCUMENTS

| JP | 2016-526412 A | 9/2016 | |
|----|----|----|----|
| JP | 2018-105954 A | 7/2018 | |
| WO | 2014/181568 | 11/2014 | |
| WO | WO-2016022665 A1 \* | 2/2016 | ....... B29D 11/00038 |
| WO | 2016/076523 A1 | 5/2016 | |

OTHER PUBLICATIONS

Written Opinion issued in International Patent Application No. PCT/JP2018/040650 dated Jan. 22, 2019 and English translation of same. 17 pages.

Sakhdari, M. et al., "Transparent and Self-Activated Harmonic Sensor Using Integrated Graphene Antennas and Circuits," 2016 IEEE International Symposium on Antennas and Propagation (APSURSI), Oct. 27, 2016, pp. 1167, 1168.

\* cited by examiner

[ FIG. 1 ]
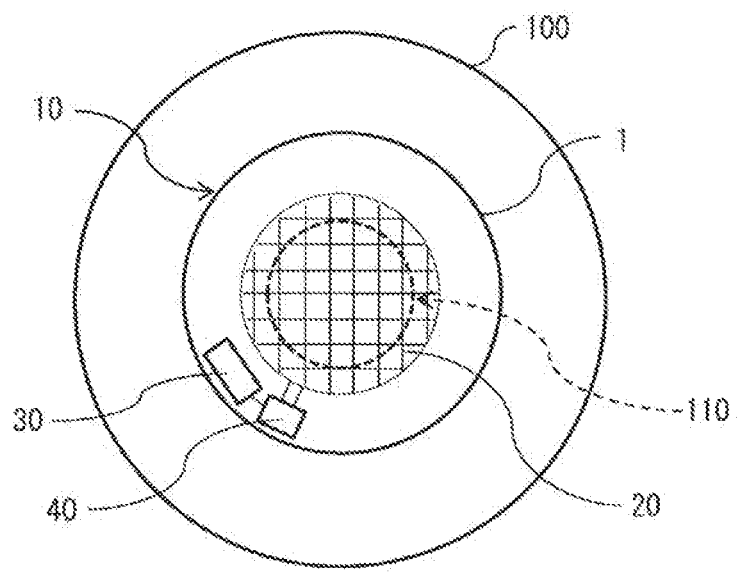
[ FIG. 2 ]
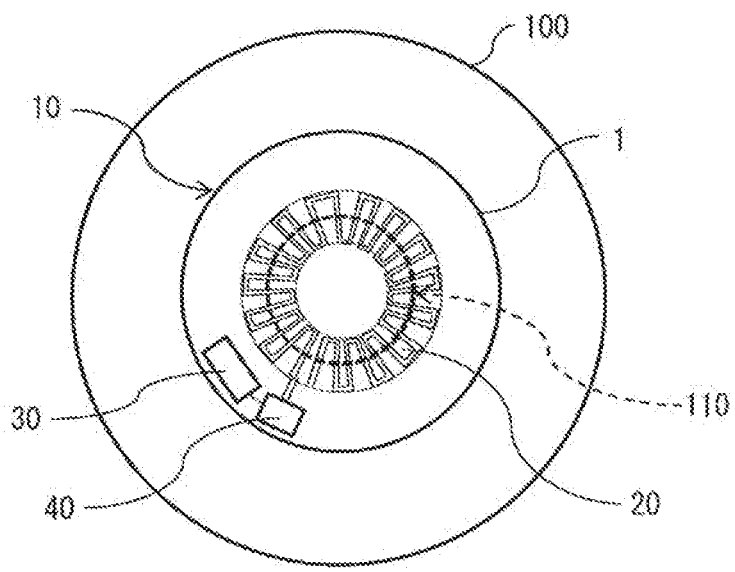

[FIG. 3]
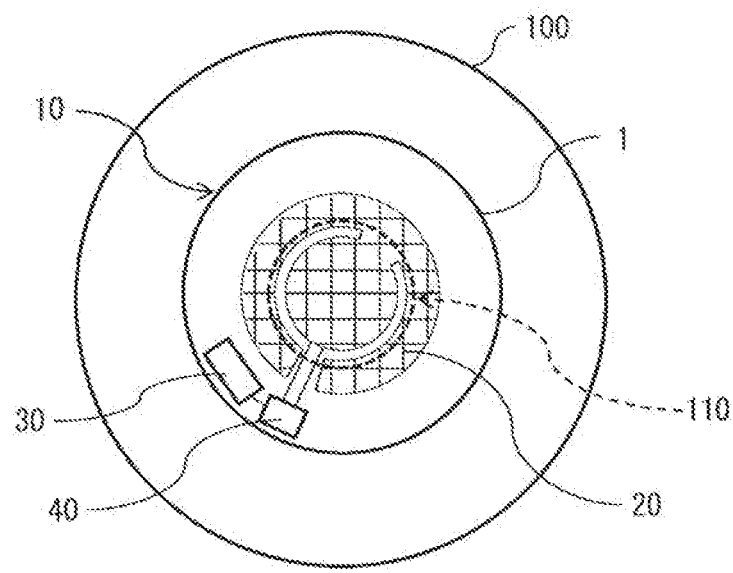
[FIG. 4]
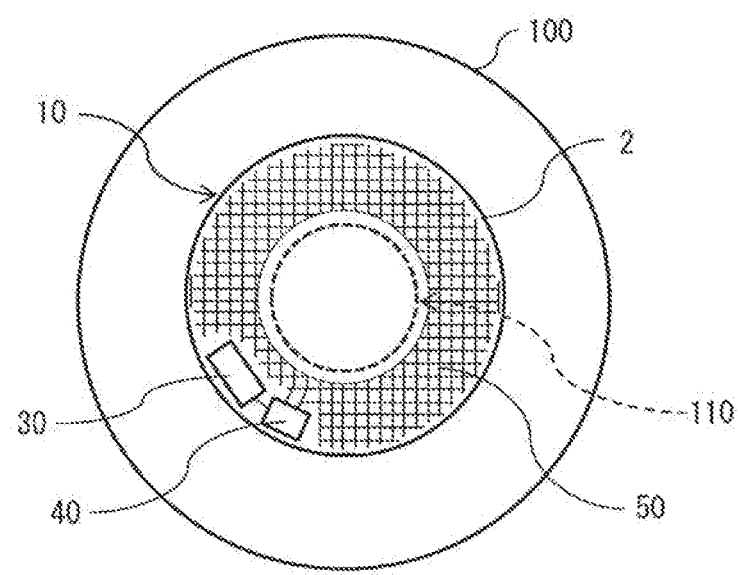

[FIG. 5]
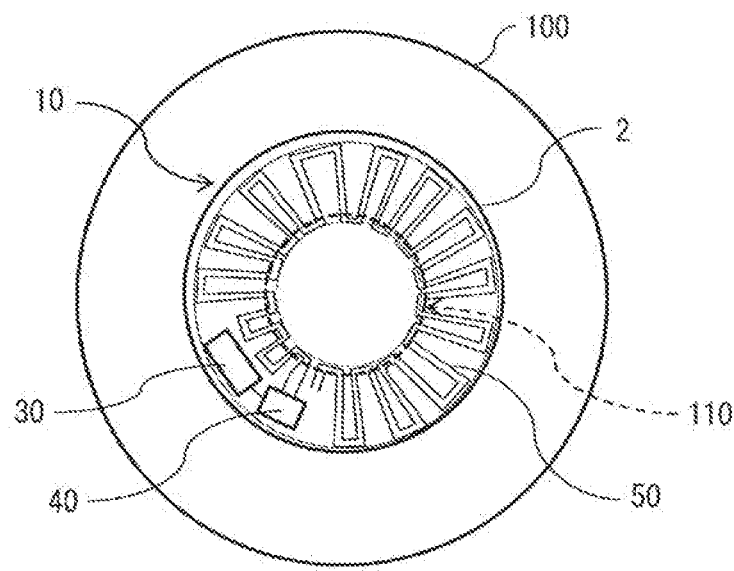
[FIG. 6]
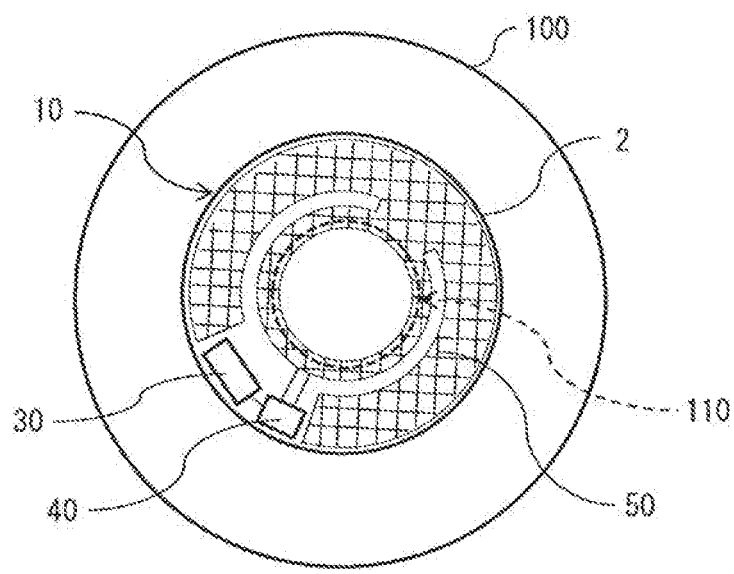

[ FIG. 7 ]
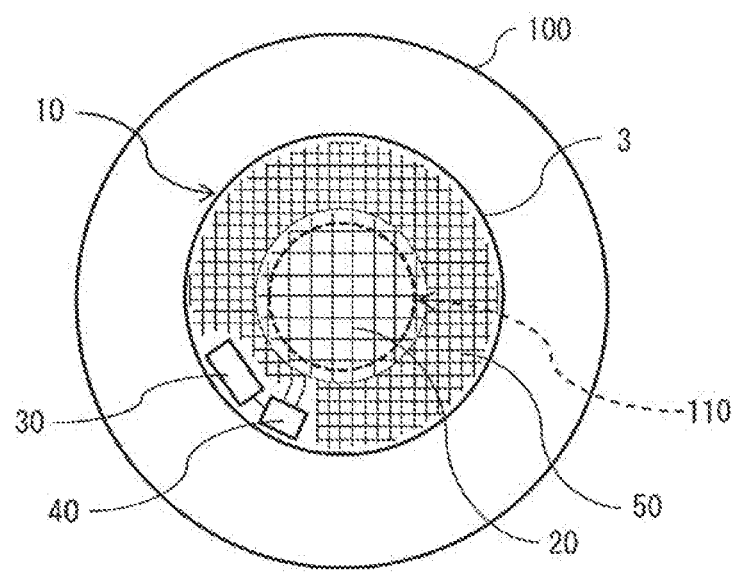
[ FIG. 8 ]
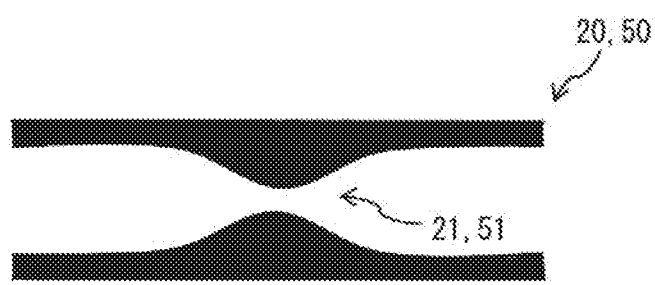
[ FIG. 9 ]
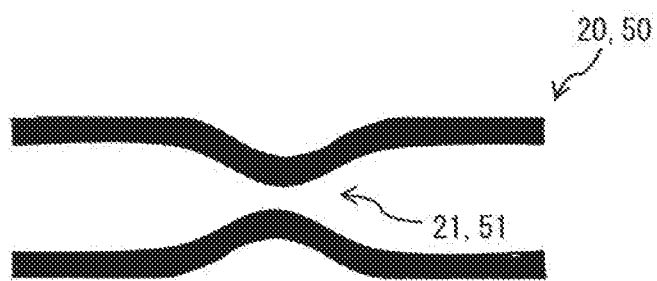

[ FIG. 10 ]
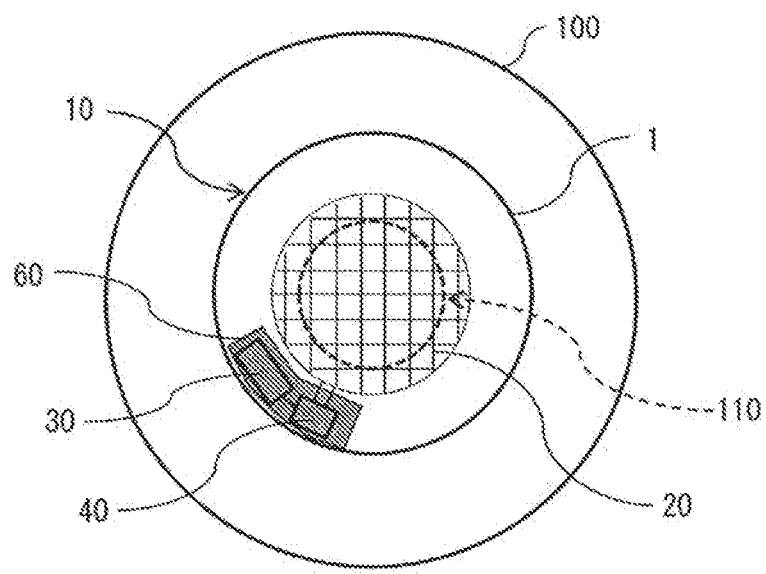
[ FIG. 11 ]
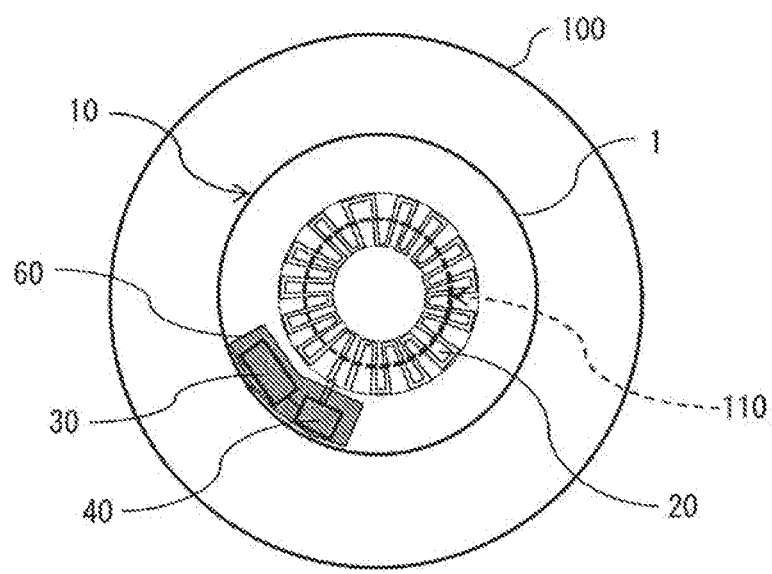

[FIG. 12]
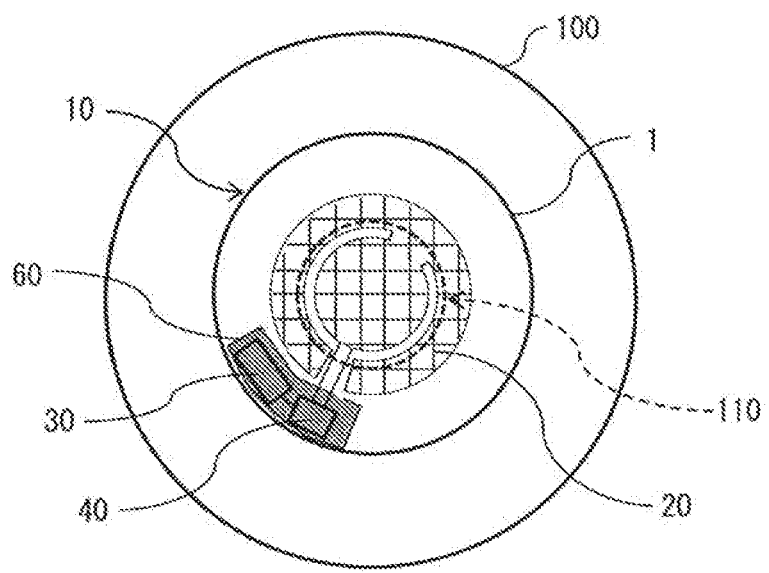
[FIG. 13]
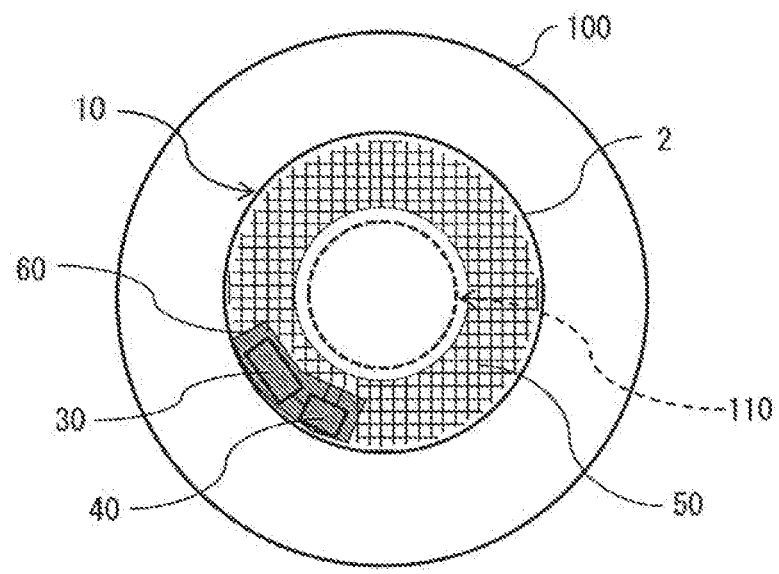

[ FIG. 14 ]
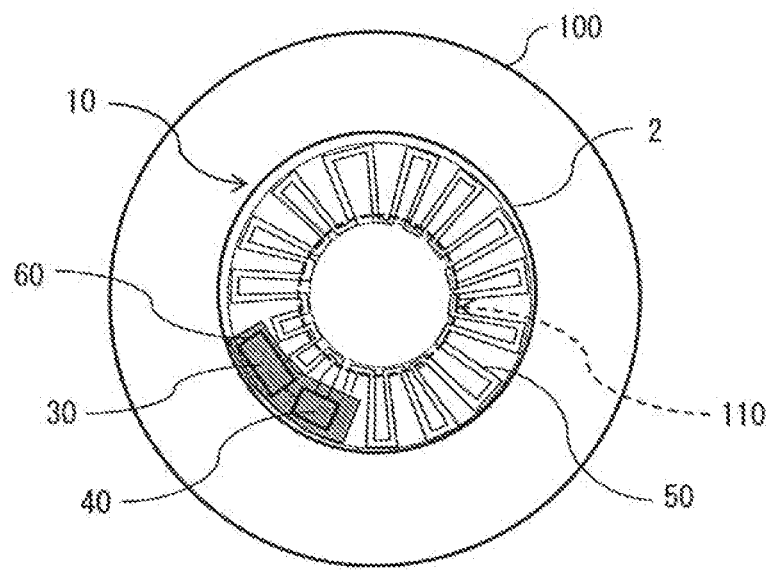
[ FIG. 15 ]
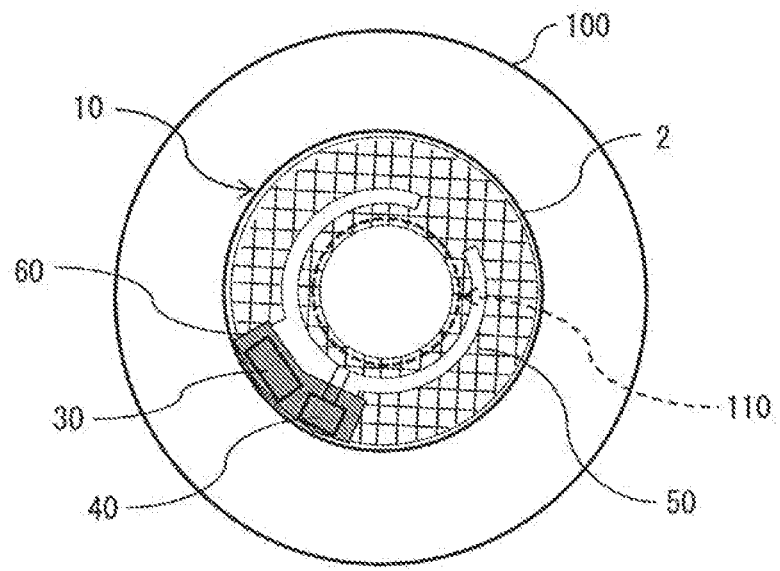

[ FIG. 16 ]
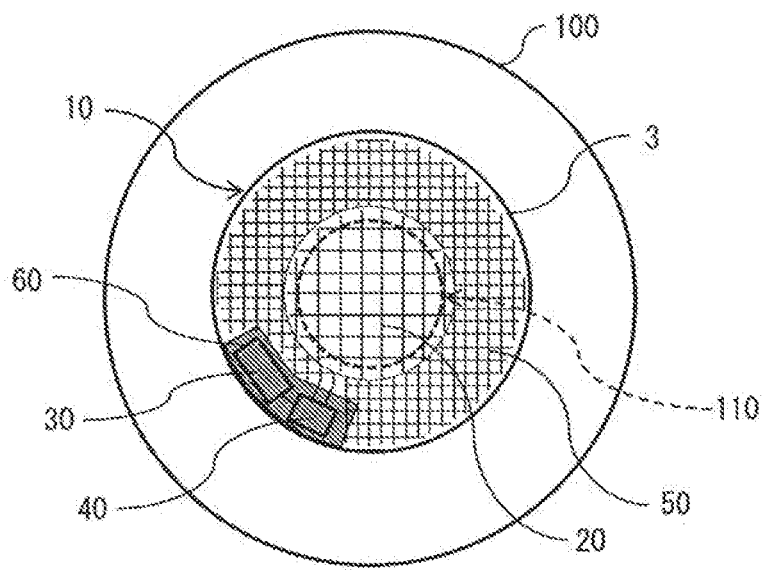
[ FIG. 17 ]
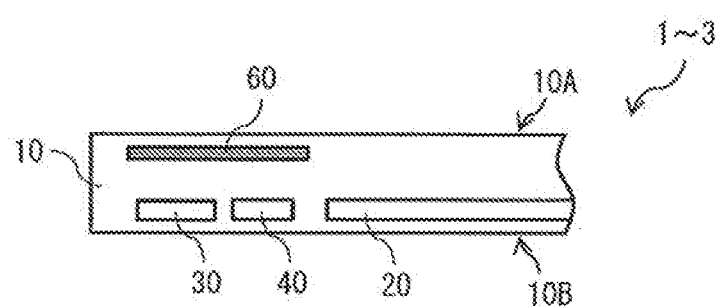
[ FIG. 18 ]
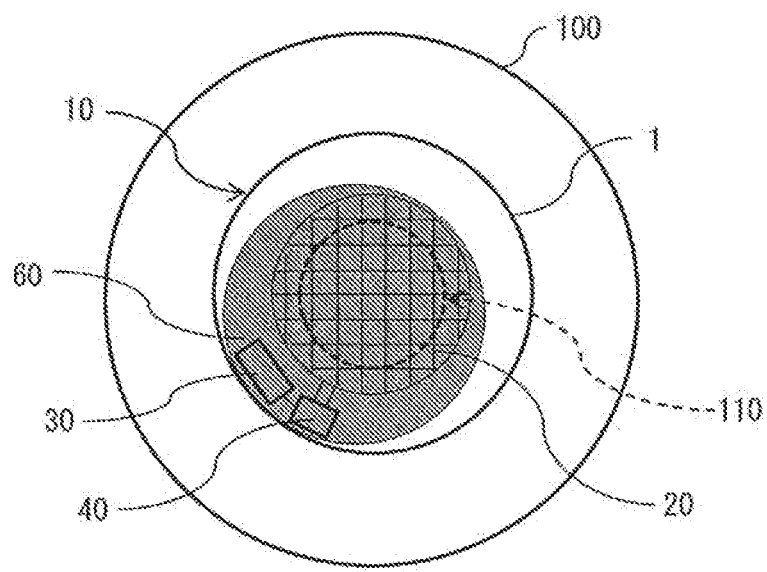

[ FIG. 19 ]
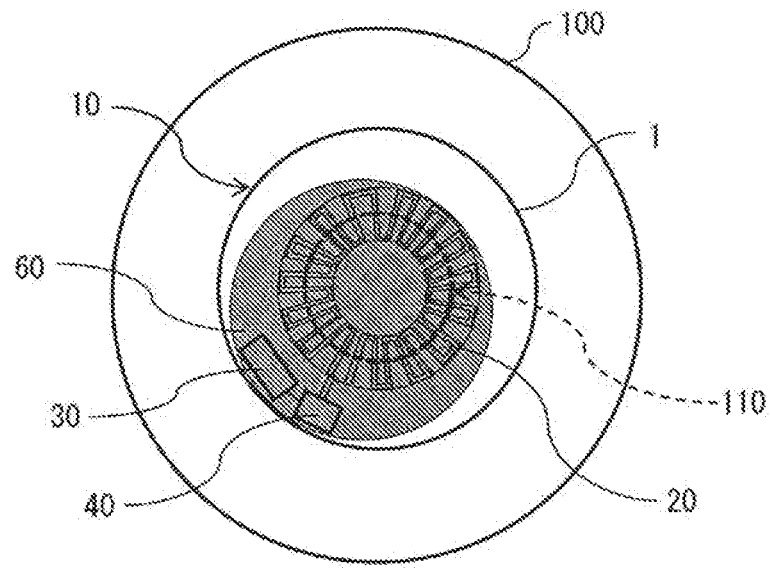
[ FIG. 20 ]
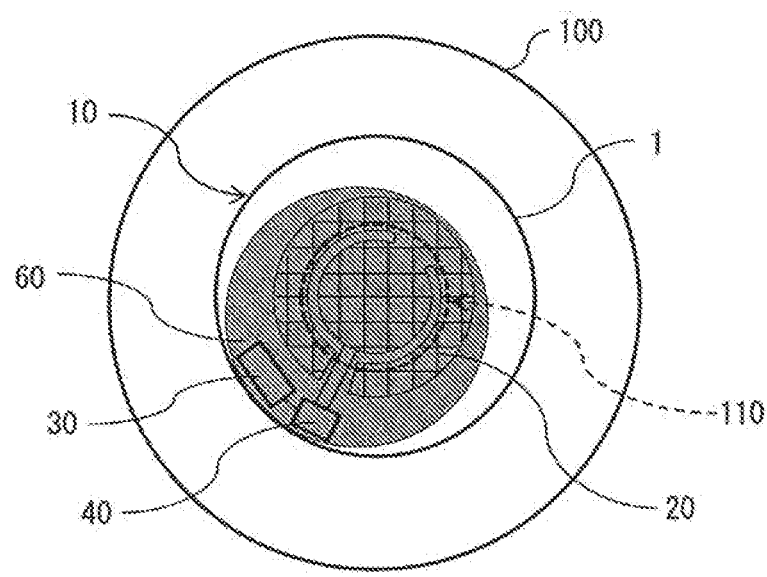

[FIG. 21]
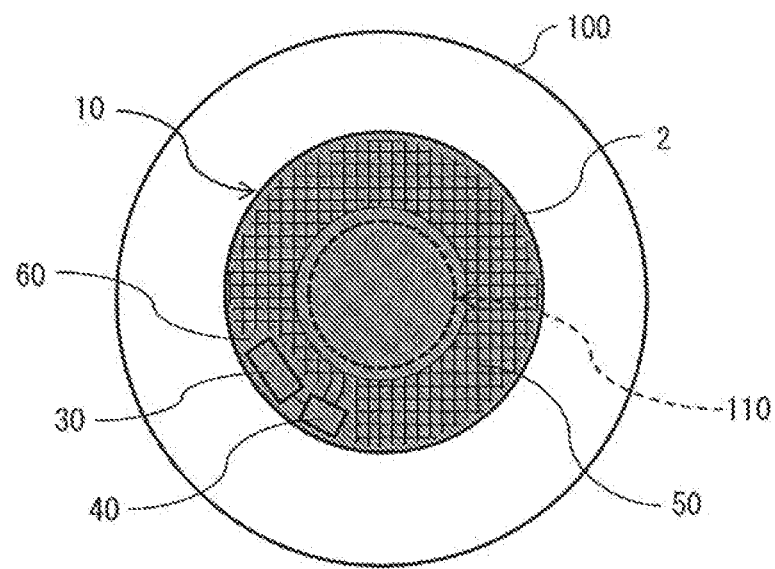
[FIG. 22]
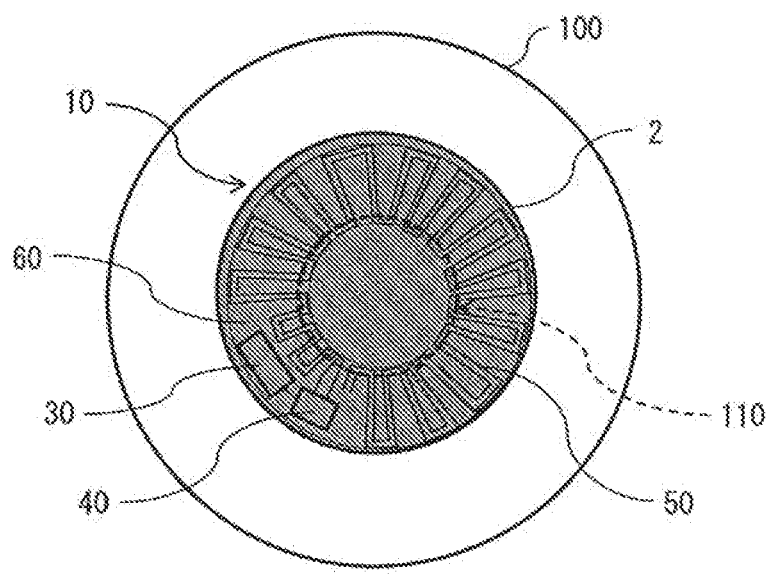

[ FIG. 23 ]
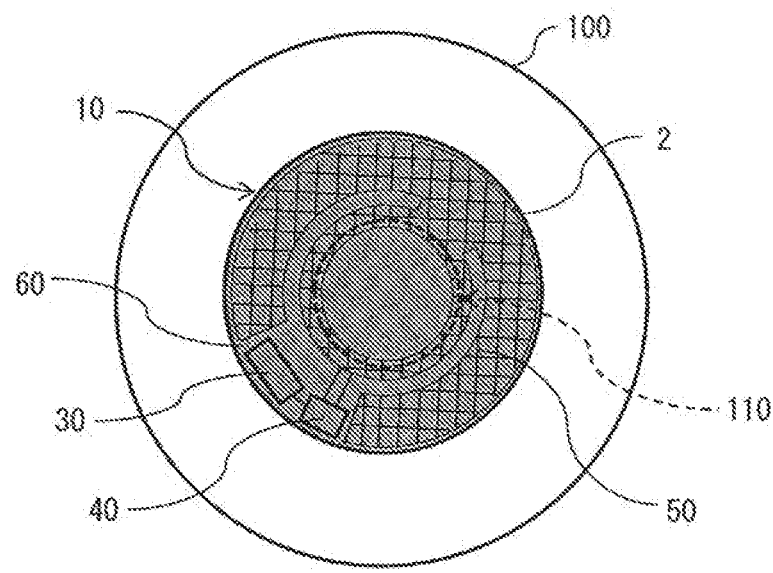
[ FIG. 24 ]
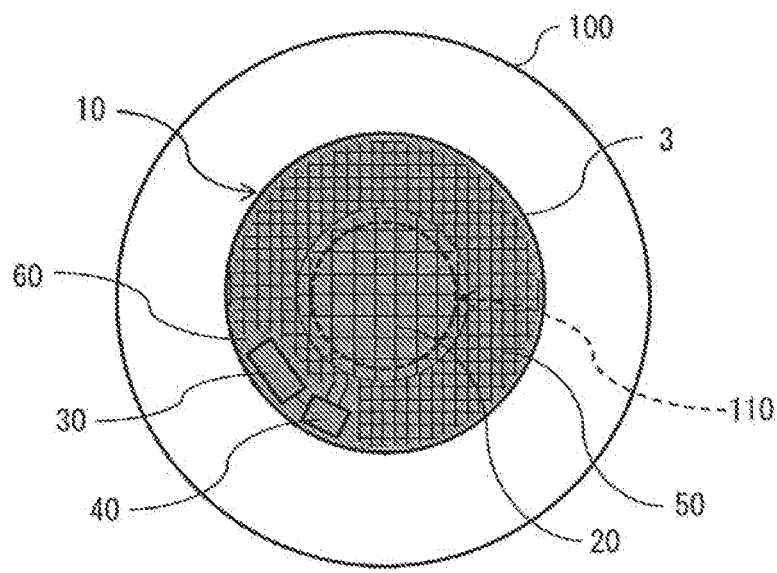
[ FIG. 25 ]
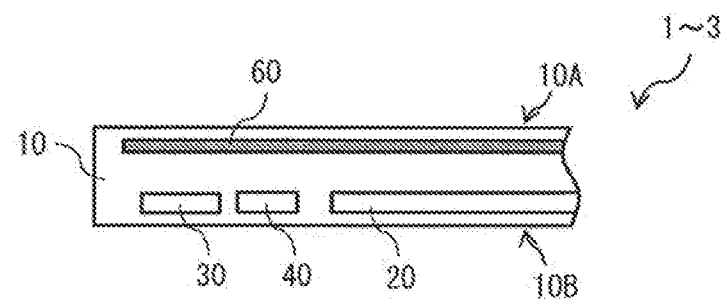

[ FIG. 26 ]
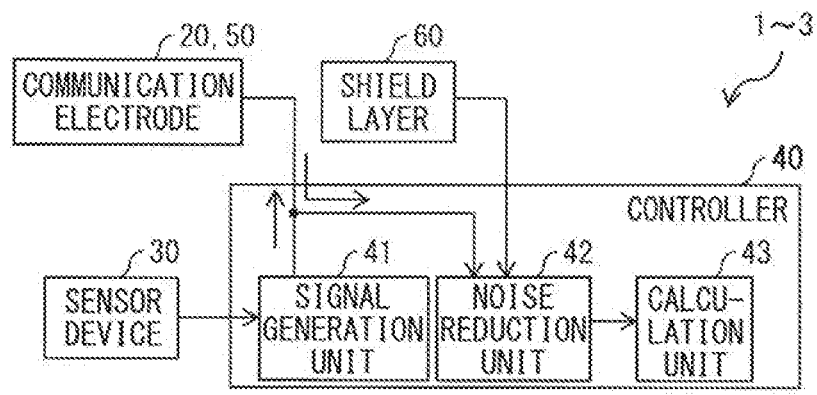
[ FIG. 27 ]
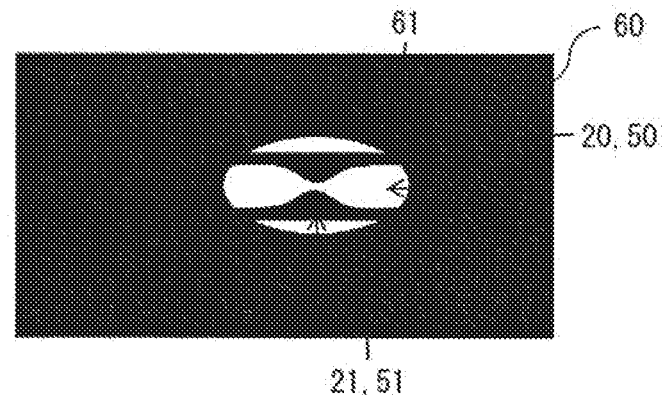
[ FIG. 28 ]
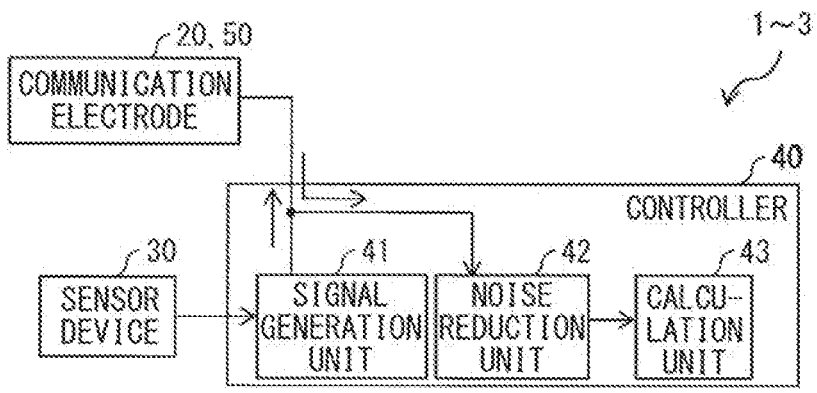

[FIG. 29]
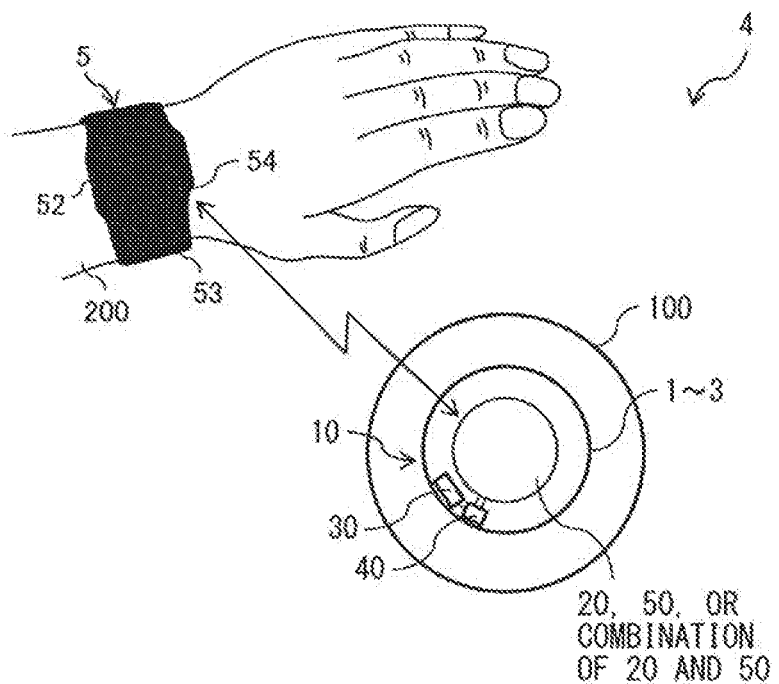
[FIG. 30]
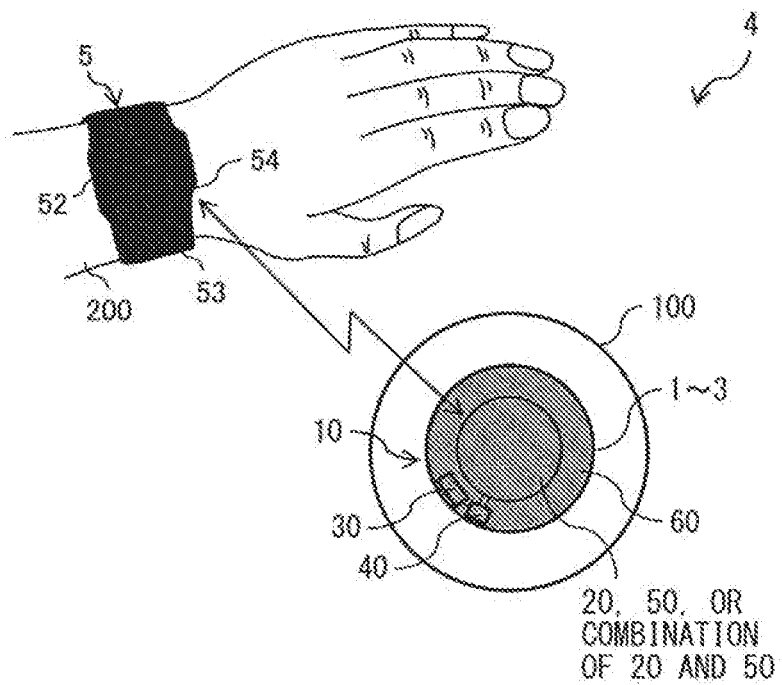

CONTACT LENS AND COMMUNICATION SYSTEM

TECHNICAL FIELD

The present disclosure relates to a contact lens and a communication system.

BACKGROUND ART

In recent years, a method of acquiring biological information or the like by means of a contact lens has been developed.

CITATION LIST

Patent Literature

PTL 1: International Publication No. WO2014/181568

SUMMARY OF THE INVENTION

Incidentally, in a case where data is transmitted from a contact lens to peripheral equipment, wireless communications are usually used. In a case where the contact lens is placed on an eyeball, communication sensitivity tends to be low and a communication speed tends to be slow because the contact lens not only has a small area but also is wet with tears. Therefore, it is desirable to provide a contact lens and a communication system that allow for improvement of the communication sensitivity and the communication speed.

A contact lens according to an embodiment of the present disclosure includes a lens unit to be placed on an eyeball and a mesh-like or meandering linear communication electrode provided in all or a portion of the lens unit.

A communication system according to an embodiment of the present disclosure includes a contact lens and a wearable apparatus. The contact lens includes a lens unit to be placed on an eyeball and a mesh-like or meandering linear first communication electrode provided in all or a portion of the lens unit. The wearable apparatus includes a second communication electrode for communication with the first communication electrode.

In the contact lens and the communication system according to the respective embodiments of the present disclosure, the mesh-like or meandering linear communication electrode is provided in the all or the portion of the lens unit. This ensures a capacity or a length of the communication electrode while suppressing degradation of visibility.

BRIEF DESCRIPTION OF DRAWINGS

FIG. 1 is a front view of an example of how a contact lens according to a first embodiment of the present disclosure is placed on an eyeball.

FIG. 2 is a front view of a modification example of how the contact lens of FIG. 1 is placed on the eyeball.

FIG. 3 is a front view of a modification example of how the contact lens of FIG. 1 is placed on the eyeball.

FIG. 4 is a front view of a modification example of how a contact lens according to a second embodiment of the present disclosure is placed on an eyeball.

FIG. 5 is a front view of a modification example of how the contact lens of FIG. 4 is placed on the eyeball.

FIG. 6 is a front view of a modification example of how the contact lens of FIG. 4 is placed on the eyeball.

FIG. 7 is a front view of an example of how a contact lens according to a third embodiment of the present disclosure is placed on an eyeball.

FIG. 8 is a view of an example of a plane configuration or a cross-sectional configuration of a communication electrode of FIG. 1 to FIG. 7.

FIG. 9 is a view of an example of the plane configuration or the cross-sectional configuration of the communication electrode of FIG. 1 to FIG. 7.

FIG. 10 is a front view of an example of how the contact lens of FIG. 1 or the contact lens of FIG. 1 in which the communication electrode of FIG. 8 and FIG. 9 is provided is placed on the eyeball.

FIG. 11 is a front view of an example of how the contact lens of FIG. 2 or the contact lens of FIG. 2 in which the communication electrode of FIG. 8 and FIG. 9 is provided is placed on the eyeball.

FIG. 12 is a front view of an example of how the contact lens of FIG. 3 or the contact lens of FIG. 3 in which the communication electrode of FIG. 8 and FIG. 9 is provided is placed on the eyeball.

FIG. 13 is a front view of an example of how the contact lens of FIG. 4 or the contact lens of FIG. 4 in which the communication electrode of FIG. 8 and FIG. 9 is provided is placed on the eyeball.

FIG. 14 is a front view of an example of how the contact lens of FIG. 5 or the contact lens of FIG. 5 in which the communication electrode of FIG. 8 and FIG. 9 is provided is placed on the eyeball.

FIG. 15 is a front view of an example of how the contact lens of FIG. 6 or the contact lens of FIG. 6 in which the communication electrode of FIG. 8 and FIG. 9 is provided is placed on the eyeball.

FIG. 16 is a front view of an example of how the contact lens of FIG. 7 or the contact lens of FIG. 7 in which the communication electrode of FIG. 8 and FIG. 9 is provided is placed on the eyeball.

FIG. 17 is a view of an example of a cross-sectional configuration of the contact lens of FIG. 10 to FIG. 16.

FIG. 18 is a front view of an example of how the contact lens of FIG. 1 or the contact lens of FIG. 1 in which the communication electrode of FIG. 8 and FIG. 9 is provided is placed on the eyeball.

FIG. 19 is a front view of an example of how the contact lens of FIG. 2 or the contact lens of FIG. 2 in which the communication electrode of FIG. 8 and FIG. 9 is provided is placed on the eyeball.

FIG. 20 is a front view of an example of how the contact lens of FIG. 3 or the contact lens of FIG. 3 in which the communication electrode of FIG. 8 and FIG. 9 is provided is placed on the eyeball.

FIG. 21 is a front view of an example of how the contact lens of FIG. 4 or the contact lens of FIG. 4 in which the communication electrode of FIG. 8 and FIG. 9 is provided is placed on the eyeball.

FIG. 22 is a front view of an example of how the contact lens of FIG. 5 or the contact lens of FIG. 5 in which the communication electrode of FIG. 8 and FIG. 9 is provided is placed on the eyeball.

FIG. 23 is a front view of an example of how the contact lens of FIG. 6 or the contact lens of FIG. 6 in which the communication electrode of FIG. 8 and FIG. 9 is provided is placed on the eyeball.

FIG. 24 is a front view of an example of how the contact lens of FIG. 7 or the contact lens of FIG. 7 in which the communication electrode of FIG. 8 and FIG. 9 is provided is placed on the eyeball.

FIG. 25 is a view of an example of a cross-sectional configuration of the contact lens of FIG. 18 to FIG. 24.

FIG. 26 is a view of an example of functional blocks of the contact lens of FIG. 10 to FIG. 25.

FIG. 27 is a view of an example of a shield layer of FIG. 10 to FIG. 25.

FIG. 28 is a view of an example of functional blocks of the contact lens of FIG. 1 to FIG. 9.

FIG. 29 is a view of an example of a schematic configuration of a communication system according to a fourth embodiment of the present disclosure.

FIG. 30 is a view of an example of a schematic configuration of the communication system of FIG. 29.

MODES FOR CARRYING OUT THE INVENTION

In the following, some embodiments of the present disclosure are described in detail with reference to the drawings. It is to be noted that description is given in the following order.

1. First Embodiment
   An example in which a communication electrode is provided at a middle of a lens unit (FIG. 1)
2. Modification Examples of First Embodiment
   Variations of the communication electrode (FIG. 2 and FIG. 3)
3. Second Embodiment
   An example in which a communication electrode is provided at an outer edge of a lens unit (FIG. 4)
4. Modification Examples of Second Embodiment
   Variations of the communication electrode (FIG. 5 and FIG. 6)
5. Third Embodiment
   An example in which a communication electrode is provided at each of a middle and an outer edge of a lens unit (FIG. 7)
6. Modification Examples Common to Respective Embodiments
   Modification Example A: An example in which a narrowed section is provided in a communication electrode (FIG. 8 and FIG. 9)
   Modification Example B: An example in which a shield layer is provided on a sensor device and a controller (FIG. 10 to FIG. 17)
   Modification Example C: An example in which a shield layer is provided on a communication electrode (FIG. 18 to FIG. 25)
   Modification Example D: An example in which a shield layer is used as a communication electrode for noise removal (FIG. 26)
   Modification Example E: An example in which an opening is provided on a shield layer (FIG. 27)
   Modification Example F: An example in which the noise removal is performed without shield layer (FIG. 28)
7. Fourth Embodiment
   An example in which communications are performed between a contact lens and a wearable apparatus (FIG. 29 and FIG. 30)

1. First Embodiment

[Configuration]

Description is given of a contact lens 1 according to a first embodiment of the present disclosure. FIG. 1 illustrates an example of how the contact lens 1 is placed on an eyeball 100. The contact lens 1 performs near field communications (specifically, wireless communications of an electric field method or a radio wave method) with external equipment via a human body or a space in close proximity of the human body. The wireless communications of the electric field method refer to wireless communications that employ an electric field generated via an electrode. In contrast, the wireless communications of the radio wave method refer to wireless communications that employ, for example, a dipole antenna, a monopole antenna, a microstrip antenna, a patch antenna, a loop antenna, a slot antenna, or the like.

The eyeball 100 has a pupil 110, for example. The pupil 110 contracts under a bright environment and expands in a dark environment. The contact lens 1 includes a lens unit 10 placed on the eyeball 100 and a communication electrode 20 provided in the lens unit 10. The contact lens 1 further includes a sensor device 30 and a controller 40.

The controller 40 supplies electric power to the communication electrode 20 and outputs, to the communication electrode 20, a signal corresponding to information acquired by the sensor device 30. The controller 40 includes a processor, a storage unit, and a power supply, for example. The power supply supplies the electric power to the communication electrode 20. The storage unit includes, for example, a nonvolatile memory and includes, for example, an EEPROM (Electrically Erasable Programmable Read-Only Memory), a flash memory, a resistance variable memory, or the like. The storage unit stores a processing program to be executed by the controller 40, or the like. The processing program is a program for acquiring detection data from the sensor device 30 or outputting the acquired detection data to the external equipment via the communication electrode 20. The detection data is data obtained by utilizing the contact lens 1 and specifically is information detected by the sensor device 30. The processor executes, for example, the processing program stored in the storage unit. A function of the processor is implemented by, for example, the processor executing the processing program. The processor outputs the information (detection data) acquired by the sensor device 30 to the external equipment via the communication electrode 20.

For example, the sensor device 30 acquires biological information of a user who wears the contact lens 1. The sensor device 30 is a device that detects specific constituents (salinity, oxygen, lipid, blood glucose level, or a hormonal substance, for example) included in tears, for example. In this case, the detection data obtained by being detected by the sensor device 30 is information regarding the constituents of the tears. It is to be noted that the sensor device 30 may be, for example, a device that detects a line of sight, a device that detects a state of a blood vessel in the eyeball, a device that detects a pulse of the blood vessel in the eyeball, a device that detects an intraocular pressure, or a device that detects opening or closing of an eyelid. In a case where the sensor device 30 is the device that detects the line of sight, the detection data is the biological information regarding the line of sight. In a case where the sensor device 30 is the device that detects the state of the blood vessel in the eyeball, the detection data is the information regarding the blood vessel in the eyeball. In a case where the sensor device 30 is the device that detects the pulse of the blood vessel in the eyeball, the detection data is the information regarding the pulse of the blood vessel in the eyeball. In a case where the sensor device 30 is the device that detects the intraocular pressure, the detection data is the biological information regarding the intraocular pressure. In a case where the sensor device 30 is the device that detects the opening or closing of the eyelid, the detection data is the biological information regarding the opening or the closing of the eyelid. The sensor device 30 may be configured to acquire any information other than the biological information. The sensor device 30 may be, for example, a device that detects brightness of outside, a device that detects vibration, or a device that detects a temperature. In a case where the sensor device 30 is the device that detects the brightness of the outside, the detection data is information regarding the brightness of the outside. In a case where the sensor device 30 is the device that detects the vibration, the detection data is information regarding the vibration. In a case where the sensor device 30 is the device that detects the temperature, the detection data is information regarding the temperature.

The lens unit 10 has a curved shape that follows a surface shape of the eyeball 100. When viewed from a front, the lens unit 10 has a circular shape, for example. A diameter of the lens unit 10 has a larger value than a diameter of the pupil 110 when the pupil 110 expands under the dark environment. The lens unit 10 may be a lens having a vision correction capability for correcting myopia, hyperopia, astigmatism, or the like, or a light transmissive base material not having such a vision correction capability. The lens unit 10 includes a light transmissive resin, for example, and has a role as a supporting base material that supports the communication electrode 20.

The communication electrode 20 is formed at a middle of the lens unit 10, for example. The communication electrode 20 is mainly provided at least in a region facing the pupil 110 that contracts while being in the bright environment when the lens unit 10 is placed on the eyeball 100. That is, the communication electrode 20 is provided, for example, at least at a position that generally covers the region facing the pupil 110 that contracts while being in the bright environment. The communication electrode 20 is provided, for example, within the lens unit 10.

The communication electrode 20 includes a plurality of wiring lines that is adjacent to each other via a predetermined gap. The communication electrode 20 has the mesh-like shape, as illustrated in FIG. 1, for example. The communication electrode 20 includes, for example, a transparent conductive wiring line including an ITO (Indium Tin Oxide), an ITiO (Indium Titanium Oxide), an IZO (Indium Zinc Oxide), or a carbon nanotube. It is to be noted that the communication electrode 20 may include a conductive carbon wiring line or a metal wiring line. In addition, it is preferable that the communication electrode 20 include a wiring line that includes a low-reflectance material (material having a lower reflectance than the reflectance of a metal material) on a surface to avoid blocking of the line of sight. The communication electrode 20 may include a wiring line that includes the low-reflectance material (material having the lower reflectance than the reflectance of the metal material). The communication electrode 20 may include a wiring line in which at least one face of a top face, a side face, or a bottom face of a layer, which includes a relatively high-reflectance material, is covered by a layer that includes a relatively low-reflectance material. Examples of the low-reflectance materials, which are usable in the communication electrode 20, include a carbon nanotube or the like. An aperture ratio of the communication electrode 20 is set to cause a light transmittance of the contact lens 1 to fall within an allowable range. The aperture ratio is a proportion of a region that occupies the region facing the pupil 110 and where the communication electrode 20 is not formed.

[Effects]

In the following, description is given of effects of the contact lens 1 according to the present embodiment.

In a case where data is transmitted from the contact lens to peripheral equipment, wireless communications are usually used. In a case where the contact lens is placed on the eyeball, communication sensitivity tends to be low and a communication speed tends to be slow because the contact lens not only has a small area but also is wet with the tears. For example, in the wireless communications of the radio wave method, only with a thin antenna (loop antenna, or the like, for example) formed on the outer edge of the contact lens, the communication sensitivity is still low and the communication speed is slow. In addition, for example, in the wireless communications of the electric field method, only with a thin antenna electrode (loop-shaped electrode, or the like, for example) formed on the outer edge of the contact lens, the communication sensitivity is still low and the communication speed is slow.

In contrast, in the present embodiment, the mesh-like communication electrode 20 is provided in a portion of the lens unit 10. This makes it possible to suppress deterioration of the visibility due to the communication electrode 20, as compared to a case where a plate-like communication electrode is provided. Moreover, it is possible to suppress the deterioration of the visibility due to the communication electrode 20, thus allowing the communication electrode 20 to be provided also at the middle of the lens unit 10. This makes it possible to occupy a wide region that allows for formation of the communication electrode 20, thus making it possible to ensure a capacity or a length of the communication electrode 20. As a result, improvement of the communication sensitivity or the communication speed is possible.

In addition, in the present embodiment, the communication electrode 20 is mainly provided in the region facing the pupil 110 when the lens unit 10 is placed on the eyeball 100. This makes it possible to occupy the wide region that allows for formation of the communication electrode 20, thus making it possible to ensure the capacity or the length of the communication electrode 20. As a result, the improvement of the communication sensitivity or the communication speed is possible.

In addition, in the present embodiment, the communication electrode 20 includes the transparent conductive wiring line including the ITO, the ITiO, the IZO, or the carbon nanotube. This makes it possible to suppress the deterioration of the visibility even if the aperture ratio of the communication electrode 20 is not so high. Moreover, the communication electrode 20 includes the transparent conductive wiring line, thus allowing the communication electrode 20 to be provided also at the middle of the lens unit 10. This makes it possible to occupy the wide region that allows for formation of the communication electrode 20, thus making it possible to ensure the capacity or the length of the communication electrode 20. As a result, the improvement of the communication sensitivity or the communication speed is possible.

In addition, in the present embodiment, the electric power is supplied from the controller 40 to the communication electrode 20 and the signal corresponding to the information acquired by the sensor device 30 is outputted from the controller 40 to the communication electrode 20. This allows the external equipment to utilize the information acquired by the sensor device 30.

2. Modification Examples of First Embodiment

In the following, description is given of modification examples of the contact lens 1 according to the aforementioned first embodiment.

Modification Example 1-1

The communication electrode 20 may have a meandering linear shape, as illustrated in FIG. 2, for example. At this time, the communication electrode 20 may include a plurality of wiring lines adjacent to each other via a narrow gap so that electric field intensity in electric field communications is large, for example. It is to be noted that in FIG. 2, although the communication electrode 20 has the shape in which the plurality of wiring lines meanders to surround a center of the lens unit 10, a wiring pattern of the communication electrode 20 is not limited to the wiring pattern illustrated in FIG. 2.

In the present modification example, the communication electrode 20 has the meandering linear shape. This makes it possible to suppress the deterioration of the visibility due to the communication electrode 20, as compared to the case where the plate-like communication electrode is provided. Moreover, it is possible to suppress the deterioration of the visibility due to the communication electrode 20, thus allowing the communication electrode 20 to be provided also at the middle of the lens unit 10. This makes it possible to occupy the wide region that allows for formation of the communication electrode 20, thus making it possible to ensure the capacity or the length of the communication electrode 20. As a result, the improvement of the communication sensitivity or the communication speed is possible.

Modification Example 1-2

The communication electrode 20 may be a mesh-like slot antenna, as illustrated in FIG. 3, for example. This makes it possible to suppress the deterioration of the visibility due to the communication electrode 20, as compared to the case where the plate-like communication electrode is provided. Moreover, it is possible to suppress the deterioration of the visibility due to the communication electrode 20, thus allowing the communication electrode 20 to be provided also at the middle of the lens unit 10. This makes it possible to occupy the wide region that allows for formation of the communication electrode 20, thus making it possible to ensure the capacity or the length of the communication electrode 20. As a result, the improvement of the communication sensitivity or the communication speed is possible.

3. Second Embodiment

[Configuration]

In the following, description is given of a contact lens 2 according to a second embodiment of the present disclosure. FIG. 4 illustrates an example of how the contact lens 2 is placed on the eyeball 100. The contact lens 1 performs the near field communications (specifically, the wireless communications of the electric field method or the radio wave method) with the external equipment via the human body or the space in close proximity of the human body. The wireless communications of the electric field method refer to the wireless communications that employ the electric field generated via the electrode. In contrast, the wireless communications of the radio wave method refer to the wireless communications that employ, for example, the dipole antenna, the monopole antenna, the microstrip antenna, the patch antenna, the loop antenna, the slot antenna, or the like.

The contact lens 2 includes a lens unit 10 to be placed on the eyeball 100 and a communication electrode 50 provided in the lens unit 10. The contact lens 2 further includes a sensor device 30 and a controller 40. The controller 40 supplies the electric power to the communication electrode 50 and outputs, to the communication electrode 50, a signal corresponding to information acquired by the sensor device 30. The controller 40 has a similar configuration to the configuration of the controller 40 according to the aforementioned embodiment.

The communication electrode 50 is formed on, for example, an outer edge of the lens unit 10. The communication electrode 50 is mainly provided at least in a region other than the region facing the pupil 110 that contracts while being in the bright environment when the lens unit 10 is placed on the eyeball 100. That is, the communication electrode 20 is provided, for example, at least avoiding the region facing the pupil 110 that contracts while being in the bright environment. The communication electrode 50 may be mainly provided in the region other than the region facing the pupil 110 that expands while being in the dark environment when the lens unit 10 is placed on the eyeball 100. At this time, the communication electrode 20 is provided, for example, avoiding the region facing the pupil 110 that expands while being in the dark environment. The communication electrode 50 is provided, for example, within the lens unit 10.

The communication electrode 50 includes the plurality of wiring lines adjacent to each other via a predetermined gap. The communication electrode 50 has a mesh-like shape, as illustrated in FIG. 4, for example. The communication electrode 50 includes the conductive carbon wiring line or the metal wiring line. It is to be noted that the communication electrode may include the transparent conductive wiring line including the ITO, the ITiO, the IZO, or the carbon nanotube. In a case where the communication electrode 50 is not formed in a region that blocks the vision, the aperture ratio of the communication electrode 50 is not limited in particular. The aperture ratio is the proportion of a region that occupies the region not facing the pupil 110 and where the communication electrode 20 is not formed. It is to be noted that in a case where the communication electrode 50 is also formed in the region that may block the vision, the aperture ratio is set to cause the light transmittance of the contact lens 2 to fall within the allowable range.

[Effects]

In the following, description is given of the effects of the contact lens 2 according to the present embodiment.

In the present embodiment, the mesh-like communication electrode 50 is provided in a portion of the lens unit 10. This makes it possible to suppress the deterioration of the visibility due to the communication electrode 50, as compared to the case where the plate-like communication electrode is provided. Moreover, it is possible to suppress the deterioration of the visibility due to the communication electrode 50, thus allowing the communication electrode 50 to be provided also in the region that may block the vision. This makes it possible to occupy the wide region that allows for formation of the communication electrode 50, thus making it possible to ensure the capacity or the length of the communication electrode 50. As a result, the improvement of the communication sensitivity or the communication speed is possible.

In addition, in the present embodiment, the communication electrode 50 is mainly provided in the region not facing the pupil 110 when the lens unit 10 is placed on the eyeball 100. This makes it possible to occupy the wide region that allows for formation of the communication electrode 50, thus making it possible to ensure the capacity or the length of the communication electrode 50. As a result, the improvement of the communication sensitivity or the communication speed is possible.

In addition, in the present embodiment, in a case where the communication electrode 50 includes the conductive carbon wiring line or the metal wiring line, it is possible to increase the capacity of the communication electrode 50, as compared to the case where the communication electrode 50 includes the transparent conductive material such as the ITO. As a result, the improvement of the communication sensitivity or the communication speed is possible.

In addition, in the present embodiment, the electric power is supplied from the controller 40 to the communication electrode 50 and the signal corresponding to the information acquired by the sensor device 30 is outputted from the controller 40 to the communication electrode 50. This allows the external equipment to utilize the information acquired by the sensor device 30.

4. Modification Examples of Second Embodiment

In the following, description is given of the modification examples of the contact lens 2 according to the aforementioned second embodiment.

Modification Example 2-1

The communication electrode 50 may have the meandering linear shape, as illustrated in FIG. 5, for example. At this time, the communication electrode 50 may include the plurality of wiring lines adjacent to each other via the narrow gap so that the electric field intensity in the electric field communications is large, for example. It is to be noted that in FIG. 5, although the communication electrode 50 has the shape in which the plurality of wiring lines meanders to surround the center of the lens unit 10, the wiring pattern of the communication electrode 50 is not limited to the wiring pattern illustrated in FIG. 5.

In the present modification example, the communication electrode 50 has the meandering linear shape. This makes it possible to suppress the deterioration of the visibility due to the communication electrode 50, as compared to the case where the plate-like communication electrode is provided. In addition, it is possible to suppress the deterioration of the visibility due to the communication electrode 50, thus allowing the communication electrode 50 to be provided also in the region that may block the visibility. This makes it possible to occupy the wide region that allows for formation of the communication electrode 50, thus making it possible to ensure the capacity or the length of the communication electrode 50. As a result, the improvement of the communication sensitivity or the communication speed is possible.

Modification Example 2-2

The communication electrode 50 may be the mesh-like slot antenna, as illustrated in FIG. 6, for example. This makes it possible to suppress the deterioration of the visibility due to the communication electrode 50, as compared to the case where the plate-like communication electrode is provided. Moreover, it is possible to suppress the deterioration of the visibility due to the communication electrode 50, thus allowing the communication electrode 50 to be provided also in the region that may block the vision. This makes it possible to occupy the wide region that allows for formation of the communication electrode 50, thus making it possible to ensure the capacity or the length of the communication electrode 50. As a result, the improvement of the communication sensitivity or the communication speed is possible.

5. Third Embodiment

[Configuration]

In the following, description is given of a contact lens 3 according to a third embodiment of the present disclosure. FIG. 7 illustrates an example of how the contact lens 3 is placed on the eyeball 100. The contact lens 3 performs the near field communications (specifically, the wireless communications of the electric field method or the radio wave method) with the external equipment via the human body or the space in close proximity of the human body. The wireless communications of the electric field method refer to the wireless communications that employ the electric field generated via the electrode. In contrast, the wireless communications of the radio wave method refer to the wireless communications that employ, for example, the dipole antenna, the monopole antenna, the microstrip antenna, the patch antenna, the loop antenna, the slot antenna, or the like.

The contact lens 3 includes a lens unit 10 to be placed on the eyeball 100 and a communication electrode 20 and a communication electrode 50 provided in the lens unit 10. The contact lens 3 further includes a sensor device 30 and a controller 40. The communication electrode 20 (first partial electrode) is the communication electrode 20 according to the aforementioned first embodiment and the modification examples thereof and is mainly provided in the region facing the pupil 110 when the lens unit 10 is placed on the eyeball 100. On the other hand, the communication electrode 50 (second partial electrode) is the communication electrode 50 according to the aforementioned second embodiment and the modification examples thereof, and is mainly provided in the region other than the region facing the pupil 110 when the lens unit 10 is placed on the eyeball 100. In the present embodiment, the aperture ratio of the communication electrode 20 is larger than the aperture ratio of the communication electrode 50, for example. It is to be noted that the aperture ratio of the communication electrode 20 may be equal to the aperture ratio of the communication electrode 50.

[Effects]

In the following, description is given of effects of the contact lens 3 according to the present embodiment.

In the present embodiment, the communication electrode 20 according to the aforementioned first embodiment and the modification examples thereof and the communication electrode 50 according to the aforementioned second embodiment and the modification examples thereof are provided in the lens unit 10. This makes it possible to suppress the deterioration of the visibility due to the communication electrodes 20 and 50, as compared to the case where the plate-like communication electrode is provided. Moreover, it is possible to suppress the deterioration of the visibility due to the communication electrodes 20 and 50, thus allowing the communication electrodes 20 and 50 to be provided also in the region that may block the vision. This makes it possible to occupy the wide region that allows for formation of the communication electrodes 20 and 50, thus making it possible to ensure the capacity or the length of the communication electrodes 20 and 50. As a result, the improvement of the communication sensitivity or the communication speed is possible.

6. Modification Examples Common to Respective Embodiments

In the following, description is given of modification examples common to the respective embodiments.

Modification Example A

FIG. 8 and FIG. 9 illustrate an example of a plane configuration or a cross-sectional configuration of the communication electrodes 20 and 50 according to the aforementioned respective embodiments and the modification examples thereof. In the aforementioned respective embodiments and the modification examples thereof, the communication electrodes 20 and 50 each include the plurality of wiring lines adjacent to each other via the predetermined gap. At this time, the plurality of wiring lines that configures the communication electrode 20 has a narrowed section 21 where the gap is locally narrowed. The plurality of wiring lines that configures the communication electrode 50 has a narrowed section 51 where the gap is locally narrowed. In the narrowed sections 21 and 51, a wiring line width is thick locally, as illustrated in FIG. 8, for example. In the narrowed sections 21 and 51, the wiring line may locally undulate to the proximate wiring line side, as illustrated in FIG. 9, for example. In a case where the gap is narrowed locally in this manner, the electric field intensity becomes intense locally in the narrowed section 51. Consequently, the electric field generated in the narrowed section 51 propagates farther than an electric field generated in a location other than the narrowed section 51 in each of the communication electrodes 20 and 50.

In the present modification example, the narrowed section 51 is provided in each of the communication electrodes 20 and 50. This causes the electric field generated in the narrowed section 51 to propagate farther than the electric field generated in the location other than the narrowed section 51 in each of the communication electrodes 20 and 50. Thus, it is possible to lengthen a distance allowing the contact lenses 1 to 3 to each communicate with the external equipment. In addition, the intensity of the electric field generated in the narrowed section 51 is larger than the intensity of the electric field generated in the location other than the narrowed section 51 in each of the communication electrodes 20 and 50. Thus, it is possible to stabilize the communications between each of the contact lenses 1 to 3 and the external equipment.

Modification Example B

FIG. 10 to FIG. 17 illustrate modification examples of the contact lenses 1 to 3 according to the aforementioned respective embodiments and the modification examples thereof. FIG. 10 illustrates an example of how the contact lens 1 of FIG. 1 or the contact lens 1 of FIG. 1 in which the communication electrode 20 of FIG. 8 and FIG. 9 is provided is placed on the eyeball. FIG. 11 illustrates an example of how the contact lens 1 of FIG. 2 or the contact lens 1 of FIG. 2 in which the communication electrode 20 of FIG. 8 and FIG. 9 is provided is placed on the eyeball. FIG. 12 illustrates an example of how the contact lens 1 of FIG. 3 or the contact lens 1 of FIG. 3 in which the communication electrode 20 of FIG. 8 and FIG. 9 is provided is placed on the eyeball. FIG. 13 illustrates an example of how the contact lens 2 of FIG. 4 or the contact lens 2 of FIG. 4 in which the communication electrode 20 of FIG. 8 and FIG. 9 is provided is placed on the eyeball. FIG. 14 illustrates an example of how the contact lens 2 of FIG. 5 or the contact lens 2 of FIG. 5 in which the communication electrode 20 of FIG. 8 and FIG. 9 is provided is placed on the eyeball. FIG. 15 illustrates an example of how the contact lens 2 of FIG. 6 or the contact lens 2 of FIG. 6 in which the communication electrode 20 of FIG. 8 and FIG. 9 is provided is placed on the eyeball. FIG. 16 illustrates an example of how the contact lens 3 of FIG. 7 or the contact lens 3 of FIG. 7 in which the communication electrode 20 of FIG. 8 and FIG. 9 is provided is placed on the eyeball. FIG. 17 illustrates an example of the cross-sectional configuration of each of the contact lenses 1 to 3 of FIG. 10 to FIG. 16.

In the aforementioned respective embodiments and the modification examples thereof, each of the contact lenses 1 to 3 may further include a shield layer 60. The shield layer 60 prevents entry of an electric field or a magnetic field from the outside. In the present modification example, the shield layer 60 is provided on a position that faces the sensor device 30, the controller 40, or both and that is located on side opposite to the eyeball 100 in a positional relation to the sensor device 30 or the controller 40. The shield layer 60 is provided, for example, within the lens unit 10. The shield layer 60 includes a conductive material. The shield layer 60 includes the conductive carbon or metal, for example. It is to be noted that the shield layer 60 may include the transparent conductive material such as the ITO, the ITiO, the IZO, or the carbon nanotube.

In the present modification example, the shield layer 60 is provided. This allows the sensor device 30 or the controller 40 to reduce an adverse impact due to the electric field or the magnetic field from the outside. Consequently, high-precision measurement by the sensor device 30 is possible.

Modification Example C

FIG. 18 to FIG. 25 illustrate modification examples of the contact lenses 1 to 3 according to the aforementioned respective embodiments and the modification examples thereof. FIG. 18 illustrates an example of how the contact lens 1 of FIG. 1 or the contact lens 1 of FIG. 1 in which the communication electrode 20 of FIG. 8 and FIG. 9 is provided is placed on the eyeball. FIG. 19 illustrates an example of how the contact lens 1 of FIG. 2 or the contact lens 1 of FIG. 2 in which the communication electrode 20 of FIG. 8 and FIG. 9 is provided is placed on the eyeball. FIG. 20 illustrates an example of how the contact lens 1 of FIG. 3 or the contact lens 1 of FIG. 3 in which the communication electrode 20 of FIG. 8 and FIG. 9 is provided is placed on the eyeball. FIG. 21 illustrates an example of how the contact lens 2 of FIG. 4 or the contact lens 2 of FIG. 4 in which the communication electrode 20 of FIG. 8 and FIG. 9 is provided is placed on the eyeball. FIG. 22 illustrates an example of how the contact lens 2 of FIG. 5 or the contact lens 2 of FIG. 5 in which the communication electrode 20 of FIG. 8 and FIG. 9 is provided is placed on the eyeball. FIG. 23 illustrates an example of how the contact lens 2 of FIG. 6 or the contact lens 2 of FIG. 6 in which the communication electrode 20 of FIG. 8 and FIG. 9 is provided is placed on the eyeball. FIG. 24 illustrates an example of how the contact lens 3 of FIG. 7 or the contact lens 3 of FIG. 7 in which the communication electrode 20 of FIG. 8 and FIG. 9 is provided is placed on the eyeball. FIG. 25 illustrates an example of the cross-sectional configuration of each of the contact lens 1 to 3 of FIG. 18 to FIG. 24.

In the aforementioned respective embodiments and the modification examples thereof, each of the contact lenses 1 to 3 may further include the shield layer 60. The shield layer 60 prevents entry of the electric field or the magnetic field from the outside. In the present modification example, the shield layer 60 is provided on a position that faces the sensor device 30, the controller 40, and the communication electrodes 20 and 50, and that is located on the side opposite to the eyeball 100 in the positional relation to the sensor device 30, the controller 40, and the communication electrodes 20 and 50. The shield layer 60 is provided, for example, within the lens unit 10. The shield layer 60 includes the conductive material. In the shield layer 60, a portion facing the communication electrode 20 includes the conductive carbon or metal, for example, and a portion facing the communication electrode 50 includes the transparent conductive material such as the ITO, the ITiO, the IZO, or the carbon nanotube, for example. It is to be noted that the shield layer 60 as a whole may include the conductive carbon or the metal. In addition, the shield layer 60 as a whole may include the transparent conductive material such as the ITO, the ITiO, the IZO, or the carbon nanotube.

In the present modification example, the shield layer 60 is provided. This allows the sensor device 30, the controller 40, and the communication electrodes 20 and 50 to reduce the adverse impact due to the electric field or the magnetic field from the outside. Consequently, the high-precision measurement by the sensor device 30 is possible. Moreover, in a case where the communication electrodes 20 and 50 include the metal material, provision of the shield layer 60 makes it possible to prevent viewing of flare due to reflections or iridescence due to diffraction at the communication electrodes 20 and 50.

Modification Example D

FIG. 26 illustrates an example of functional blocks of each of the contact lenses 1 to 3 according to the aforementioned modification examples B and C. In the contact lenses 1 to 3 according to the aforementioned modification examples B and C, the controller 40 may include a signal generation unit 41, a noise reduction unit 42, and a calculation unit 43, for example. The signal generation unit 41 generates a signal corresponding to information (detection signal) acquired by the sensor device 30 and outputs the generated signal to the external equipment via the communication electrodes 20 and 50. The noise reduction unit 42 acquires a signal from the external equipment via the communication electrodes 20 and 50. Using a noise signal acquired by the shield layer 60, the noise reduction unit 42 further reduces noise included in the signal acquired from the external equipment via the communication electrodes 20 and 50 and outputs a signal thereby obtained (noise reduction signal) to the calculation unit 43. The calculation unit 43 performs a calculation based on the noise reduction signal inputted from the noise reduction unit 42.

In the present modification example, the noise included in the signal acquired from the external equipment via the communication electrodes 20 and 50 is reduced by means of the noise signal acquired by the shield layer 60. Consequently, even in a case where noise due to the electric field or the magnetic field from the outside is superimposed on the signal acquired by the communication electrodes 20 and 50, use of the noise signal acquired by the shield layer 60 allows for reduction of the noise. As a result, it is possible to perform high-speed communications.

Modification Example E

FIG. 27 illustrates an example of the shield layer 60 included in each of the contact lenses 1 to 3 according to the aforementioned modification examples B, C, and D. In the contact lenses 1 to 3 according to the aforementioned modification examples B, C, and D, the communication electrodes 20 and 50 include the plurality of wiring lines adjacent to each other via the predetermined gap. At this time, the plurality of wiring lines that configures the communication electrode 20 has the narrowed section 21 where the gap is locally narrowed. The plurality of wiring lines that configures the communication electrode 50 has the narrowed section 51 where the gap is locally narrowed. The shield layer 60 has an opening 61 at a location facing the narrowed section 51, as illustrated in FIG. 27, for example. This allows for output of the electric field generated in the narrowed section 51 to the outside via the opening 61. This also makes it possible to receive the electric field from the outside at the narrowed section 51 (communication electrode 20) via the opening 61. As a result, the communications between each of the contact lenses 1 to 3 and the external equipment is possible via the space in close proximity to the human body.

Modification Example F

FIG. 28 illustrates an example of functional blocks of each of the contact lenses 1 to 3 according to the aforementioned respective embodiments and Modification Example A. In each of the contact lenses 1 to 3 according to the aforementioned respective embodiments and Modification Example A, the controller 40 may include a signal generation unit 41, a noise reduction unit 42, and a calculation unit 43, for example. The signal generation unit 41 generates a signal corresponding to the information (detection signal) acquired by the sensor device 30 and outputs the generated signal to the external equipment via the communication electrodes 20 and 50. The noise reduction unit 42 acquires the signal from the external equipment via the communication electrodes 20 and 50. For example, the noise reduction unit 42 reduces noise included in a data signal on the basis of a signal (noise signal A) acquired via the communication electrodes 20 and 50 in a period during which no communications are performed with the external equipment, and a signal (data signal B) acquired from the external equipment via the communication electrodes 20 and 50 in a period during which the communications are performed with the external equipment. The noise reduction unit 42 reduces the noise included in the data signal B by, for example, removing the noise signal A from the data signal B. The noise reduction unit 42 outputs to the calculation unit 43 the signal (noise reduction signal) obtained by, for example, reducing the noise included in the data signal B. The calculation unit 43 performs the calculation based on the noise reduction signal inputted from the noise reduction unit 42.

In the present modification example, the noise included in the data signal B, which is acquired from the external equipment via the communication electrodes 20 and 50, is reduced by means of the noise signal A obtained via the communication electrodes 20 and 50. Consequently, even in a case where the noise due to the electric field or the magnetic field from the outside is superimposed on the signal acquired by the communication electrodes 20 and 50, it is possible to reduce the noise included in the data signal B. As a result, it is possible to perform the high-speed communications.

In the present modification example, noise included in the detection signal obtained from the sensor device 30 may be reduced. For example, the signal generation unit 41 reduces noise included in a data signal D on the basis of a detection signal (noise signal C) obtained from the sensor device 30 in a period during which the sensor device 30 does not function as a sensor, and a detection signal (data signal D) acquired from the sensor device 30 in a period during which the sensor device 30 functions as the sensor. The signal generation unit 41 reduces the noise included in the data signal D by, for example, removing the noise signal C from the data signal D. The signal generation unit 41 outputs the signal obtained by, for example, reducing the noise included in the data signal D, to the external equipment via the communication electrodes 20 and 50.

In the present modification example, the noise included in the detection signal (data signal D) acquired from the sensor device 30 in the period during which the sensor device 30 functions as the sensor is reduced by means of the detection signal (noise signal C) obtained from the sensor device 30 in a period during which the sensor device 30 does not function as the sensor. Consequently, even in a case where the noise due to the electric field or the magnetic field from the outside is superimposed on the detection signal obtained from the sensor device 30, it is possible to reduce the noise included in the data signal D. As a result, it is possible to perform high-speed communications.

7. Fourth Embodiment

[Configuration]

In the following, description is given of a communication system 4 according to a fourth embodiment of the present disclosure. FIG. 29 and FIG. 30 illustrate an example of a schematic configuration of the communication system 4 that performs communications between each of the contact lenses 1 to 3 according to the aforementioned respective embodiments and the modification examples thereof and a wearable apparatus 5. The communication system 4 includes each of the contact lenses 1 to 3 according to the aforementioned respective embodiments and the modification examples thereof and the wearable apparatus 5.

FIG. 29 exemplarily illustrates the contact lenses 1 to 3 on each of which no shield layer 60 is provided. FIG. 30 exemplarily illustrates the contact lenses 1 to 3 on each of which the shield layer 60 is provided to cover the sensor device 30, the controller 40, and the communication electrode 20, the communication electrode 50, or the communication electrodes 20 and 50. It is to be noted that in FIG. 30, it is not necessary for the shield layer 60 to cover the communication electrode 20, the communication electrode 50, or the communication electrodes 20 and 50. The communication electrode 20, the communication electrode 50, or the communication electrodes 20 and 50 each correspond to a specific example of a "first communication electrode" of the present disclosure.

The wearable apparatus 5 is a wearable apparatus of a wrist band type or a watch type. The wearable apparatus 5 includes, for example, a communication electrode 54 for communications with each of the contact lenses 1 to 3, a housing 52 that stores the communication electrode 54, and a wrist securing belt 53 that supports the housing 52. The communication electrode 54 corresponds to a specific example of a "second communication electrode" of the present disclosure.

In the present embodiment, the communication electrode 20, the communication electrode 50, or the communication electrodes 20 and 50 is or are provided in a portion of the lens unit 10. This makes it possible to suppress the deterioration of the visibility due to the communication electrode 20, the communication electrode 50, or the communication electrodes 20 and 50, as compared to the case where the plate-like communication electrode is provided. Moreover, it is possible to suppress the deterioration of the visibility due to the communication electrode 20, the communication electrode 50, or the communication electrodes 20 and 50, thus allowing the communication electrode 20 to be provided also at the middle of the lens unit 10 or the communication electrode 50 to be provided in a periphery thereof. This makes it possible to occupy the wide region that allows for formation of the communication electrode 20, the communication electrode 50, or the communication electrodes 20 and 50, thus making it possible to ensure the capacity or the length of the communication electrode 20, the communication electrode 50, or the communication electrodes 20 and 50. As a result, the improvement of the communication sensitivity or the communication speed is possible.

It is to be noted that the effects described herein are merely illustrative. The effects of the present disclosure are not limited to the effects described herein. The present disclosure may have any effects other than the effects described herein.

Moreover, the present disclosure may have the following configurations, for example.

(1)

A contact lens including:

a lens unit to be placed on an eyeball; and a mesh-like or meandering linear communication electrode provided in all or a portion of the lens unit.

(2)

The contact lens according to (1), in which the communication electrode is mainly provided in a region facing a pupil when the lens unit is placed on the eyeball.

(3)

The contact lens according to (2), in which the communication electrode includes a transparent conductive wiring line.

(4)

The contact lens according to (2), in which the communication electrode includes a wiring line including a low-reflectance material, or a wiring line in which at least one face of a top face, a side face, or a bottom face of a layer including a high-reflectance material is covered by a layer including a low-reflectance material.

(5)

The contact lens according to (1), in which the communication electrode is mainly provided in a region other than a region facing a pupil when the lens unit is placed on the eyeball.

(6)

The contact lens according to (5), in which the communication electrode includes a conductive carbon wiring line or a metal wiring line.

(7)

The contact lens according to (1), in which the communication electrode includes a first partial electrode and a second partial electrode, the first partial electrode being mainly provided in a region facing a pupil when the lens unit is placed on the eyeball, the second partial electrode being mainly provided in a region other than the region facing the pupil when the lens unit is placed on the eyeball, and an aperture ratio of the first partial electrode is larger than an aperture ratio of the second partial electrode.

(8)

The contact lens according to any one of (1) to (7), in which the communication electrode includes a plurality of wiring lines adjacent to each other via a predetermined gap, and the plurality of wiring lines has a narrowed section in which the gap is locally narrow.

(9)

The contact lens according to any one of (1) to (8), further including:

a sensor device; and a controller that supplies electric power to the communication electrode and outputs a signal corresponding to information acquired by the sensor device to the communication electrode.

(10)

A communication system including a contact lens and a wearable apparatus, in which the contact lens includes a lens unit to be placed on an eyeball and a mesh-like or meandering linear first communication electrode provided in all or a portion of the lens unit, and the wearable apparatus includes a second communication electrode for communication with the first communication electrode.

With the contact lens and the communication system according to the respective embodiments of the present disclosure, the capacity or the length of the communication electrode is ensured while the deterioration of the visibility is suppressed. Consequently, it is possible to improve the communication sensitivity or the communication speed. It is to be noted that the effects of the present disclosure are not necessarily limited to the effects described here, and any effect described in the present specification may be provided.

This application claims the benefits of Japanese Priority Patent Application JP2017-240264 filed with the Japan Patent Office on Dec. 15, 2017, the entire contents of which are incorporated herein by reference.

It should be understood by those skilled in the art that various modifications, combinations, sub-combinations and alternations may occur depending on design requirements and other factors insofar as they are within the scope of the appended claims or the equivalents thereof.

The invention claimed is:

1. A contact lens comprising:

a lens unit to be placed on an eyeball; and a mesh-like or meandering linear communication electrode provided in all or a portion of the lens unit, wherein the communication electrode comprises a first partial electrode and a second partial electrode, the first partial electrode being mainly provided in a region facing a pupil when the lens unit is placed on the eyeball, the second partial electrode being mainly provided in a region other than the region facing the pupil when the lens unit is placed on the eyeball, and an aperture ratio of the first partial electrode is larger than an aperture ratio of the second partial electrode.

2. The contact lens according to claim 1, wherein the communication electrode is mainly provided in the region facing the pupil when the lens unit is placed on the eyeball.

3. The contact lens according to claim 2, wherein the communication electrode includes a transparent conductive wiring line.

4. The contact lens according to claim 2, wherein the communication electrode includes a wiring line including a low-reflectance material, or a wiring line in which at least one face of a top face, a side face, or a bottom face of a layer including a high-reflectance material is covered by a layer including a low-reflectance material.

5. The contact lens according to claim 1, wherein the communication electrode includes a conductive carbon wiring line or a metal wiring line.

6. The contact lens according to claim 1, wherein the communication electrode includes a plurality of wiring lines adjacent to each other via a predetermined gap, and the plurality of wiring lines has a narrowed section in which the gap is locally narrow.

7. The contact lens according to claim 1, further comprising:

a sensor device; and a controller that supplies electric power to the communication electrode and outputs a signal corresponding to information acquired by the sensor device to the communication electrode.

8. A communication system comprising a contact lens and a wearable apparatus, wherein the contact lens includes a lens unit to be placed on an eyeball and a mesh-like or meandering linear first communication electrode provided in all or a portion of the lens unit, and the wearable apparatus includes a second communication electrode for communication with the first communication electrode, wherein the first communication electrode comprises a first partial electrode and a second partial electrode, the first partial electrode being mainly provided in a region facing a pupil when the lens unit is placed on the eyeball, the second partial electrode being mainly provided in a region other than the region facing the pupil when the lens unit is placed on the eyeball, and an aperture ratio of the first partial electrode is larger than an aperture ratio of the second partial electrode.

* * * * *